(12) United States Patent
Carlton et al.

(10) Patent No.: US 11,293,005 B2
(45) Date of Patent: Apr. 5, 2022

(54) PROCESS FOR MAKING MINERALIZED MYCELIUM SCAFFOLDING AND PRODUCT MADE THEREBY

(71) Applicant: Ecovative Design LLC, Green Island, NY (US)

(72) Inventors: Alex Carlton, Troy, NY (US); Gavin McIntyre, Troy, NY (US)

(73) Assignee: Ecovative Design LLC, Green Island, NY (US)

( * ) Notice: Subject to any disclaimer, the term of this patent is extended or adjusted under 35 U.S.C. 154(b) by 112 days.

(21) Appl. No.: 16/397,326

(22) Filed: Apr. 29, 2019

(65) Prior Publication Data

US 2019/0338240 A1    Nov. 7, 2019

Related U.S. Application Data

(60) Provisional application No. 62/667,793, filed on May 7, 2018.

(51) Int. Cl.
C12N 1/14    (2006.01)

(52) U.S. Cl.
CPC ............ *C12N 1/14* (2013.01); *C12N 2533/14* (2013.01); *C12N 2533/18* (2013.01); *C12N 2533/54* (2013.01)

(58) Field of Classification Search
CPC .. C12N 1/14; C12N 2533/14; C12N 2533/18; C12N 2533/54
See application file for complete search history.

(56) References Cited

U.S. PATENT DOCUMENTS

| | | |
|---|---|---|
| 1,979,176 A | 10/1934 | Schicht |
| 2,509,984 A | 5/1950 | Morrow |
| 2,657,647 A | 11/1953 | Rapisarda |
| 2,723,493 A | 11/1955 | Stoller |
| 2,815,621 A | 12/1957 | Carter |
| 2,964,070 A | 12/1960 | Linhardt |
| 3,268,606 A | 8/1966 | Jaeger |
| 3,316,592 A | 5/1967 | Forrest |
| 3,317,375 A | 5/1967 | Molinet et al. |
| 3,421,554 A | 1/1969 | Carter |
| 3,477,558 A | 11/1969 | Fleischauer |
| 3,499,261 A | 3/1970 | Hullhorst et al. |
| 3,708,952 A | 1/1973 | Schulze et al. |
| 3,717,953 A | 2/1973 | Kuhn et al. |
| 3,782,033 A | 1/1974 | Hickerson |
| 3,810,327 A | 5/1974 | Giansante |
| 3,828,470 A | 8/1974 | Stoller |
| 3,961,938 A | 6/1976 | Iizuka et al. |
| 4,027,427 A | 6/1977 | Stoller et al. |
| 4,036,122 A | 7/1977 | Langen |
| 4,038,807 A | 8/1977 | Beardsley et al. |
| 4,063,383 A | 12/1977 | Green |
| 4,073,956 A | 2/1978 | Yates |
| 4,127,965 A | 12/1978 | Mee |
| 4,136,767 A | 1/1979 | Sarovich |
| 4,226,330 A | 10/1980 | Butler |
| 4,263,744 A | 4/1981 | Stoller |
| 4,265,915 A | 5/1981 | MacLennan et al. |
| 4,294,929 A | 10/1981 | Solomons et al. |
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |
| 5,030,425 A | 7/1991 | Bowers-Irons et al. |
| 5,074,959 A | 12/1991 | Yamanaka et al. |
| 5,085,998 A | 2/1992 | Lebron et al. |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |

(Continued)

FOREIGN PATENT DOCUMENTS

| | | |
|---|---|---|
| CN | 1059662 A | 3/1992 |
| CN | 1732887 A | 2/2006 |

(Continued)

OTHER PUBLICATIONS

Cha et al., "Biomimetic synthesis of ordered silica structures mediated by block copolypeptides". Nature (2000) 403(6767): 289-292.
Kerem et al., "Chemically defined solid-state fermentation of Pleurotus Ostreatus". Enzyme Microbiol Tech. 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.

(Continued)

*Primary Examiner* — Ruth A Davis
(74) *Attorney, Agent, or Firm* — Knobbe, Martens, Olson & Bear, LLP

(57) ABSTRACT

The process of making a mineralized mycelium scaffolding requires obtaining a scaffold of fungal biopolymer having a network of interconnected mycelia cells, functionalizing the biopolymer to create precursor sites and thereafter mineralizing the scaffold with one of silicates, apatites and carbonates. The mineralized mycelium scaffolding may be used for medical applications in place of mineralized collagen membranes and collagen/hydroxyapatite composite scaffolds.

12 Claims, No Drawings

(56) References Cited

U.S. PATENT DOCUMENTS

| | | |
|---|---|---|
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,098,677 A | 8/2000 | Wegman et al. |
| 6,112,504 A | 9/2000 | McGregor et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,444,437 B1 | 9/2002 | Sporleder et al. |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Luth et al. |
| 6,660,164 B1 | 12/2003 | Stover |
| 6,679,301 B2 | 1/2004 | Makino et al. |
| 6,726,911 B1 | 4/2004 | Jülich et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,079,978 B2 | 7/2015 | Räsänen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga et al. |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 | 1/2020 | Bayer et al. |
| 10,537,070 B2 | 1/2020 | Betts et al. |
| 10,583,626 B2 | 3/2020 | Bayer et al. |
| 10,589,489 B2 | 3/2020 | Bayer et al. |
| 10,687,482 B2 | 6/2020 | Ross et al. |
| 10,785,925 B2 | 9/2020 | McNamara et al. |
| 2001/0012235 A1 | 8/2001 | Schuchardt |
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |
| 2003/0056451 A1 | 3/2003 | Plsek et al. |
| 2003/0121201 A1 | 7/2003 | Dahlberg et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2005/0133536 A1 | 6/2005 | Kelsey et al. |
| 2005/0137272 A1 | 6/2005 | Gaserod et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 | 6/2008 | Bayer et al. |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0132314 A1 | 5/2012 | Weigel et al. |
| 2012/0135504 A1 | 5/2012 | Ross |

(56) References Cited

U.S. PATENT DOCUMENTS

| | | |
|---|---|---|
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1* | 1/2018 | Ross .................. A01G 18/10 |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0102530 A1 | 4/2020 | Winiski et al. |
| 2020/0146224 A1 | 5/2020 | Kaplan-Bie et al. |
| 2020/0157506 A1 | 5/2020 | Bayer et al. |
| 2020/0208097 A1 | 7/2020 | Winiski |
| 2020/0239830 A1 | 7/2020 | O'Brien et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0127601 A9 | 5/2021 | Kaplan-Bie et al. |
| 2021/0348117 A9 | 11/2021 | Winiski |

FOREIGN PATENT DOCUMENTS

| | | |
|---|---|---|
| CN | 101248869 A | 8/2008 |
| CN | 101653081 A | 2/2010 |
| CN | 106947702 A | 7/2017 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2875805 A1 | 5/2015 |
| EP | 2878340 A1 | 6/2015 |
| EP | 2485779 B1 | 2/2018 |
| EP | 3292769 A1 | 3/2018 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| JP | H03234889 A | 10/1991 |
| JP | H049316 A | 1/1992 |
| JP | 6111510 B1 | 4/2017 |
| KR | 20050001175 A | 1/2005 |
| KR | 101851655 B1 | 4/2018 |
| WO | WO 1999/024555 | 5/1999 |
| WO | WO 2001/087045 | 11/2001 |
| WO | WO 2005/067977 | 7/2005 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2014/039938 | 3/2014 |
| WO | WO 2014/195641 | 12/2014 |
| WO | WO 2016/149002 | 9/2016 |
| WO | WO 2017/056059 | 4/2017 |
| WO | WO 2017/120342 | 7/2017 |
| WO | WO 2017/136950 | 8/2017 |
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |

OTHER PUBLICATIONS

Monmaturapoj et al., "Influence of preparation method on hydroxyapatite porous scaffolds". Bull Mater Sci. (2011) 34(7): 1733-1737.

Manoli et al., "Crystallization of calcite on chitin". J Cryst Growth, (1997) 182(1-2): 116-124.

Passauer U. et al., "Pilze in Höhlen" [Cave Mushrooms]. Denisia (2016) 37: 211-224.

Udawatte et al., "Solidification of xonotlite fibers with chitosan by hydrothermal hot pressing". J Mater Sci. Lttrs. (2000) 45(6): 298-301.

Varma et al., "Porous calcium phosphate coating over phosphorylated chitosan film by a biomimetic method". Biomaterials (1999) 20(9): 879-884.

Weaver et al., "The stomatopod dactyl club: a formidable damage-tolerant biological hammer". Science (2012) 336(6086): 1275-1280.

Yamasaki et al., "A hydrothermal hot-pressing method: Apparatus and Application". J Mater Sci Lttrs. (1986) 5(3): 355-356.

Zivanovic et al., "Changes in Mushroom Texture and Cell Wall Composition Affected by Thermal Processing". J Food Service (2004) 69: 44-49.

Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.

Amsellem et al., "Long-term preservation of viable mycelia of two mycoherbicidal organisms". Crop Protection (1999) 18: 643-649.

Angelini et al., "Effect of antimicrobial activity of Melaleuca alternifolia essential oil on antagonistic potential of Pleurotus

(56) References Cited

OTHER PUBLICATIONS species against Trichoderma harzianum in dual culture." World J Microbiol Biotech. (2008) 24(2): 197-202.

Antón et al., "PimM, a PAS Domain Positive Regulator of Pimaricin Biosynthesis in Streptomyces natalensis." Microbiol. (2007) 153: 3174-3183.

Appels et al., "Hydrophobin gene deletion and environmental growth conditions impact mechanical properties of mycelium by affecting the density of the material." Scientific Reports (2018) 8(1): 1-7.

Arshad et al., "Tissue engineering approaches to develop cultured meat from cells: a mini review." Cogent Food & Agriculture (2017) 3(1): 1320814 in 11 pages.

Ashiuchi et al., "Isolation of Bacillus subtilis (chungkookjang), a poly-gamma-glutamate producer with high genetic competence". Appl Microbiol Biotechnol. (2011) 57: 764-769.

Bajaj et al., "Poly (glutamic acid)—An emerging biopolymer of commercial interest". Bioresource Tech. (2011) 102(10): 5551-5561.

Baysal et al., "Cultivation of oyster mushroom on waste paper with some added supplementary materials". Biosource Technology (2003) 89: 95-97.

Begum et al., "Bioconversion and saccharification of some lignocellulosic wastes by Aspergillus oryzae ITCC-4857.01 for fermentable sugar production". Elect J Biotech. (2011) (14)5: 3 in 8 pages.

Belardinelli et al., "Actions of Adenosine and Isoproterenol on Isolated Mammalian Ventricular Myocytes." Circulation Res. (1983) 53(3): 287-297.

Belay et al., "Preparation and Characterization of Graphene-agar and Graphene Oxide-agar Composites." JOAPS (2017) 134(33): 45085.

Binder et al., "Phylogenetic and phylogenomic overview of the Polyporales". Mycologia (Nov.-Dec. 2013) 105(6): 1350-1373.

Blanchette et al., "Fungal mycelial mats used as textile by indigenous people of North America", Mycologia (Feb. 20, 2021) pp. 1-7.

Booth et al., "Potential of a dried mycelium formulation of an indigenous strain of Metarhizium anisopliae against subterranean pests of cranberry." Biocontrol Science and Technology (2000) 10: 659-668.

Bormann et al., "Characterization of a Novel, Antifungal, Chitin-binding Protein from Streptomyces Tendae Tü901 that Interferes with Growth Polarity." J Bacter. (1999) 181(24): 7421-7429.

Bowman et al., "The structure and synthesis of the fungal cell wall". Bioassays (2006) 28(8): 799-808.

Bružauskaite et al., "Scaffolds and Cells for Tissue Regernation: Different Scaffold Pore Sizes—Different Cell Effects." Cytotechnology (2016) 68(3): 355-369.

Byrd, "Clean meat's path to your dinner plate", The Good Food Institute, website accessed Nov. 14, 2018, https://www.gfi.org/clean-meats-path-to-commercialization; 11 pages.

Cerimi et al., "Fungi as source for new bio-based materials: a patent review", Fungal Biol Biotechnol. (2019) 6: 17; 10 pgs.

Chai et al., "β-Glucan Synthase Gene Overexpression and β-Glucans Overproduction in Pleurotus ostreatus Using Promoter Swapping". PLoS ONE (2013) 8(4): e61693 in 7 pages.

Chaudhary et al., "Understanding rice hull ash as fillers in polymers: a review". Silicon Chemistry (2002) 1:281-289.

Chi et al., "Can Co-culturing of Two White-rot Fungi Increase Lignin Degradation and the Production of Lignin-degrading Enzymes?" Inter'l Biodeter Biodegrad. (2007) 59(1):32-39.

Collins English Dictionary, "Mould", retrieved from http://collinsdictionary.com/dictionary/english/mould, archived on Apr. 8, 2015, 3 pages.

Dias et al., "Synthesis and characterization of chitosan-polyvinyl alcohol-bioactive glass hybrid membranes". Biomatter (2011) 1(1): 114-119.

Elleuche et. al., "Carbonic anhydrases in fungi". Microbiology (2010) 156: 23-29.

Elsacker et al., "Growing living and multifunctional mycelium composites for large-scale formwork applications using robotic abrasive wire-cutting", Construction Bldg Mater. (2021) 283: 122732 in 16 pages.

Fleet G.H., "Cell walls". in The Yeasts, by Rose et al. [Eds.] 2nd Edition. Vol. 4. London: Academic Press. (1991) pp. 199-277.

Frandsen R.J.N., "A guide to binary vectors and strategies for targeted genome modification in fungi using Agrobacterium tumefaciens-mediated transformation". J Microbiol Methods (2011) 87:247-262.

Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.

Glowacki et al., "Bioconjugation of Hydrogen-bonded Organic Semiconductors with Functional Proteins." J Mate Chem. C (2015) 3(25): 6554-6564.

Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.

Google Report, Complete colonization substrate mushroom (2 pages) Jan. 30, 2018., 2 pages.

Google Dictionary Definition "Composite", downloaded on Nov. 21, 2018; 1 page.

Gourmet Mushroom, Inc., "What is Mushroom?"—Mushroom Facts Mushroom Information—Educational & Science Projects (2004). Downloaded from www.gmushrooms.com, on Nov. 27, 2017; 5 pages.

Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.

Greetham et al., "Pheotypic characterisation of Saccharomyces sensu stricto to Inhibitory Compounds Released During the Deconstruction of Lignocellulosic Material." 3th International Congress on Yeasts, ICY Aug. 26-30, 2012, Madison, USA; 1 page.

Griffin et al., "Regulation of macromolecular synthesis, colony development and specific growth rate of Achlya bisexualis during balanced growth". J General Microbiol. (1974) 80(2):381-388.

Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.

Haneef et al., "Advanced Materials from Fungal Mycelium: Fabrication and Tuning of Physical Properties", Scientific Reports 7(1): 1-11; DOI: 10.1038/srep41292, Jan. 24, 2017.

Heinzkill et al., "Characterization of laccases and peroxidases from wood-rotting fungi (family Coprinaceae)." Appl Environ Microbiol. (1998) 64: 1601-1606.

Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf; 27 pages.

Home Depot "Miracle Gro® Perlite Mix", retrieved from the internet: http://homedepot.com/p/Miracle-Gro-8-pt-Perlite-Mix-74278430/204502291; 2 pages.

Home Depot "Pennington—Fast Acting Gypsum", retrieved from the internet: http://homedepot.com/p/Miracle-Gro-8-pt-Perlite-Mix-74278430/204502291; 2 pages.

Horton et al., "Regulation of Dikaryon-Expressed Genes by FRT1 in the Basidiomycete Schizophyllum commune". Fungal Genet Biol. (1999) 26(1):33-47.

Howden et al., "The effects of breathing 5% CO2 on human cardiovascular responses and tolerance to orthostatic stress". Exper. Physiol. (2004) 89(4): 465-471.

Hüttner et al., "Recent advances in the intellectual property landscape of filamentous fungi", Fungal Biol Biotechnol. (2020) 7:16; 17 pgs.

Hyde et al., "The amazing potential of fungi: 50 ways we can exploit fungi industrially". Fungal Diversity (2019) 97(1): 1-136.

(56) References Cited

OTHER PUBLICATIONS

Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.
Jones et al., "Leather-like material biofabrication using fungi", Nature Sustainability (2020) https://doi.org/10.1038/s41893-020-00606-1, Sep. 7, 2020.
Kamzolkina et al., "Micromorphological features of Pleurotus pulmonarius (Fr.) Quel. and P. ostreaturs (Jacq.) P. Kumm. Strains in pure and binary culture with yeasts". Tsitologiia (2006) 48(2): 153-160.
Kemppainen et al., "Transformation of the Mycorrhizal Fungus *Laccaria bicolor* using Agrobacterium tumefaciens." Bioengin Bugs (2011) 2(1):38-44.
Kerem et al., "Effect of Mananese on Lignin Degradation by Pleurotus ostreatus during Solid-State Fermentation". Applied and Environmental Microbiology (1993) 59(12):4115-4120.
Kilaru et al., "Investigating dominant selection markers for Coprinopsis cinerea: a carboxin resistance system and re-evaluation of hygromycin and phleomycin resistance vectors". Curr Genet. (2009) 55: 543-550.
Kim et al., "Current Technologies and Related Issues for Mushroom Transformation." Mycobiology (2015) 43(1): 1-8.
Kotlarewski et al., "Mechanical Properties of Papua New Guinea Balsa Wood." European J Wood Wood Products (2016) 74(1): 83-89.
Kück et al., "New tools for the genetic manipulation of filamentous fungi". Appl Microbiol Biotechnol. (2010) 86: 51-62.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>;2 pages.
Kuo, 2005-2006. Glossary of Mycological Terms. Mushroom Expert.Com., pp. 1-13; downloaded from http://www.mushroomexpert.com/glossary.html (May 8, 2015).
Li et al., "Preparation and Characterization of Homogeneous Hydroxyapatite/Chitosan Composite Scaffolds via In-Situ Hydration". J Biomaterials Nanobiotech. (2010) 1: 42-49.
Luo et al., "Coprinus comatus: a basidiomycete fungus forms novel spiny structures and infects nematode." Mycologia (2004) 96(6): 1218-1225.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merriam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus *Aspergillus awamori*." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.
Moore D., "Tolerance of Imprecision in Fungal Morphogenesis." In Proceedings of the 4th Meeting on the Genetics and Cellular Biology of Basidiomycetes (Mar. 1998) pp. 13-19.
Mushroom Growers' Handbook 1, "Oyster Mushroom Cultivation". Part II, Chapter 5, (2005) pp. 75-85.
Mushroom Growers' Handbook 2, "Shiitake Bag Cultivation", Part I Shiitake. Published by Mush World (2005) Chapter 4, pp. 73-90 and pp. 105-109.

Naknean et al., "Factors Affecting Retention and Release of Flavor Compounds in Food Carbohydrates." Inter'l Food Res J. (2010) 17(1): 23-34.
Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.
Norvell L., Fungi Biology. Encyclopedia.(2002); 2 pages.
Novoselova et al., "Cocultivation of Pleurotus ostreatus (Jacq.) P. Kumm. with yeasts". Moscow University Biol Sciences Bulletin (2011) 66(3): 102-105.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.
Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Peng et al., "Microbial biodegradation of polyaromatic hydrocarbons". FEMS Microbiol Rev. (2008) 32:927-955.
Perez et al., "Myxococcus xanthus induces actinorhodin overproduction and aerial mycelium formation by Streptomyces coelicolor." Microbial Biotech. (2011) 4(2): 175-183.
Philippoussis et al., "Production of Mushrooms Using Agro-Industrial Residues as Substrates", in Biotechnology for Agro-Industrial Residues, Chapter 9, (2009) pp. 163-187.
Poppe J., Mushroom Growers' Handbook 1, 2004, Part II. Chapter 5, "Substrate", pp. 80-81.
Pompei et al., "The Use of Olive Milling Waste-Water for the Culture of Mushrooms on Perlite". Acta Horticulturae (1994) 361:179-185.
Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.
Ross, P., "Pure Culture" 1997-Present; URL: <http://billhoss.phpwebhosting.com/ross/index.php?kind>; downloaded Dec. 14, 2016 in 11 pages.
Royse et al., "Influence of substrate wood-chip particle size on shiitake (*Lentinula edodes*) yield". Bioresource Tehnology (2001) 76(3): 229-233.
Sapak et al., "Effect of endophytic bacteria on growth and suppression of Tganoderma infection in oil palm". Int J Agric Biol. (2008) 10(2): 127-132.
Schaner et al., "Decellularized Vein as a Potential Scaffold for Vascular Tissue Engineering." J Vascular Surg. (2004) 40(1): 146-153.
Schirp et al., "Production and characterization of natural fiber-reinforced thermoplastic composites using wheat straw modified with the fungus *Pleurotus ostreatus*". J Appl. Polym Sci. (2006) 102:5191-5201.
Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.
Schuurman J., "Unique agar Pearls." YouTube video; Feb. 16, 2012, <https://www.youtube.com/watch?v=8GqTTOHETPQ>; 1 page.
Science Daily, May 7, 2007, retrieved from the Internet; http://www.sciencedaily.com/releases/2007/05/070506085628.htm., 3 pages.
Seamon K.B., "Forskolin: Unique Diterpene Activator of Adenylate Cyclase in Membranes and in Intact Cells." PNAS (1981) 78(6): 3363-3367.
Sinotech et al., (2015): retrieved from the Internet http://www.sinotech.com/compressionAndTransferMolding.html., 4 pages.
Slater, M. "Young SoRo Entrepreneur Develops Environmentally Friendly Insulation." The Herald of Randolph. Jun. 21, 2007, pp. 1-2.

(56) References Cited

OTHER PUBLICATIONS

Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Stamets P., "Growing Gourmet and Medicinal Mushrooms", (Undated) Chapter 21; p. 363.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78:155-166.
Sundari et al., "Freeze-drying vegetative mycelium of Laccaria fraterna and its subsequent regeneration". Biotechnology Techniques (1999) 13:491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81(4): 675-679.
Thomas et al., "Growing Orchids in Perlite". In Perlite Plant Guide, The Schundler Company 1951, pp. 1-6, downloaded from http://www.schundler.com/index.html, archived on May 11, 2015.
Timberpress—"How Do Mushrooms Grow So Quickly.", downloaded from the internet: www.timberpress.com/blog/2017/01/how-do-mushrooms-grow-so-quickly, download Feb. 27, 2018 in 7 Pages.
Ugalde U., "Autoregulatory Signals in Mycelial Fungi in The Mycota: A Comprehensive Treatise on Fungi as Experimental Systems for Basic and Applied Research". K. Esser [Ed.] Springer Publisher, 2nd Edition (2006) Chapter 11; pp. 203-213.
Universal Oil Field, "Sawdust", downloaded from universaloilfield.org on Aug. 23, 2018, 4 pages.
Vara et al., "Cloning and expression of a puromycin N-acetyl transferase gene from Streptomyces alboniger in Streptomyces lividans and *Escherichia coli*". Gene (1985) 33(22): 197-206.
Visser et al., "Pseudoxylaria as stowaway of the fungus-growing termite nest: Interaction asymmetry between Pseudoxylaria, Termitomyces and free-living relatives". Fungal Ecology (2011) 4(5): 322-332.
Volk (2003) "Tom Volk's Fungus of the Month for Oct. 1998". This month's fungus is Pleurotus ostreatus; the Oyster mushroom, pp. 1-4, downloaded from http://botit.botany.wisc.edu/toms_fungi/oct98.html on May 8, 2015.
Wang et al., "Influence of fungal elicitors on biosynthesis of natamycin by Streptomyces natalensis HW-2". Appl Microbiol Biothechnol. (2003) 97: 5527-5534.
Wikipedia, "Water gel (plain)", Wikipedia Contributors downloaded Aug. 21, 2017 in 1 Page.
Wikipedia, "Wood", downloaded on Nov. 26, 2018, 1 page.
Xiao et al., "A Water-soluble Core Material for Manufacturing Hollow Composite Sections." Comp. Structures (2017) 182: 380-390.
Yang et al., "Medicinal Mushroom *Ganoderma lucidum* as a Potent Elicitor in Production of t-Resveratrol and t-Peceatannol in Peanut Calluses". J Agric Food Chem. (2010) 58(17): 9518-9522.
Zadrazil et al., "Influence of CO2 Concentration on the Mycelium Growth of Three Pleurotus Species", European J. Appl. Microbiol., vol. 1, pp. 327-335 (1975).
Zimin et al., "The MaSuRCA genome assembler". Bioinformatics (2013) 29(21): 2669-2677.
International Search Report and Written Opinion for PCT/US2019/030168, dated Oct. 2, 2019.

Abbadi et al., "Immunocytochemical identification and localization of lipase in cells of the mycelium of Penicillium cyclopium variety", Applied Microbial Cell Physiology (1995) 42: 923-930.
Ando et al., "Cosmetic material for skin whitening - contains mushroom mycelium cultured matter and e.g. ginseng extract, chondroitin sodium sulphate and/or hyaluronic acid", WPI/THOMSON (1992-01-14), 1992(8): Accession #1992-062018; Abstract of JP4009316A; in 9 pages.
Antinori et al., "Advanced mycelium materials as potential self-growing biomedical scaffolds." Scientific reports (2021) 11(1): 1-14.
Attias et al., "Biofabrication of Nanocellulose-Mycelium Hybrid Materials", Adv Sustainable Syst. (2020) 5(2): 2000196 in 12 pages; Supporting Information in 7 pages.
Bartnicki-Garcia, "Cell wall chemistry, morphogenesis, and taxonomy of fungi", Annual Review Microbiol. (1968) 22(1): 87-108.
Borrás et al., "Trametes versicolor pellets production: Low-cost medium and scale-up", Biochem Eng J. (2008) 42(1): 61-66.
Dugdale J. "This new surf company is making boards of mushrooms". Blog post - Jun. 25, 2015.
Green et al., "Mechanical Properties of Wood", Forest Products Laboratory, 1999. in Wood Handbook- Wood as an engineering material. Gen Tech. Rep. FPL-GTR-113, Chapter 4 in 46 pages.
Halseide P., "Cutting brick the safe way". The Aberdeen Group (1988) Publication #M880354 in 2 pages.
Hidayat et al., "Characterization of polylactic acid (PLA)/kenaf composite degradation by immobilized mycelia of Pleurotus ostreatus". Inter Biodeter Biodegrad. (2012) 71: 50-54.
Highland Woodworking, "Making Thin Lumber and Veneer Out of Ordinary Boards", Sales Website (2017) in 3 pages.
Holt et al., "Biobased Composition Boards Made from Cotton Gin and Guayule Wastes: Select Physical and Mechanical Properties", Int J Mater Prod Tech. (2009) 36:104-114.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Islam et al., "Morphology and mechanics of fungal mycelium", Scientific Reports, (2017) 7(1): 1-12.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.
Jones et al., "Mycelim Composites: A Review of Engineering Characteristics and Growth Kinetics", J Bionanoscience (2017) 11 (4): 241-257.
Jones et al., "Waste-derived Low-cost Mycelium Composite Construction Materials with Improved Fire Safety", FAM (Fire and Materials) (2018) 42(7): 816-825.
Jones et al., Chitin-chitosan Thin Films from Microbiologically Upcycled Agricultural By-products. In 13th International Conference on the Mechanical Behavious of Materials, Melbourne, Australia (Jun. 2019) p. 66; in 7 pages.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Meyer et al., "Comparison of the Technical Performance of Leather, Artificial Leather, and Trendy Alternatives." Coatings (Feb. 2021) 11(2): 226; 14 pages.
Mushroom Source, "Aspen Wood Shavings for Mushroom Cultivation", Website (2015) in 2 pages.
National Institute of Health (Nih/Nibib), "Tissue Engineering and Regenerative Medicine", Retrieved Sep. 24, 2018 from https://www.nibib.nih.gov/science-education/science-topics/tissue-engineering-and-regenerative-medicine in 13 pages.

(56) References Cited

OTHER PUBLICATIONS

Pathway-27, "Beta-glucan", Aug. 2012, retrieved from http://http://www.pathway27.eu/topstory/beta-glucan/on Oct. 7, 2021 in 2 pages.
Stewart B., "Concrete Fence Posts: Fact Sheet", Texas Agriculture Extension Service, Texas A & M University (1975) Article L-1368 in 4 pages.
Trinci et al., "II. Unrestricted Growth of Fungal Mycelia", The Mycota - Growth, Differentiation and Sexuality by Wessels et al. [Eds], Springer, Berlin, Heidelberg, (1994) Chapter II: 175-193.
University of Sydney, "Competition Between Fungi". Webpage, accessed 7/16/2014-http://bugs.bio.usyd.edu.au/learning/resources/Mycology/Ecology/competition.shtml in 3 pages.
Vetchinkina et al., "Bioreduction of Gold (III) Ions from Hydrogen Tetrachloaurate..." Scientific Practical J Health Life Sciences No. 4, ISSN 22188-2268, (2013) pp. 51-56.
Wagner A. "Mycelium Biking - Eco-Design at its Best", Master's Thesis at Lulea University of Technology (2016) in 92 pages.
Wan-Mohtar et al., "The morphology of Ganoderma lucidum mycelium in a repeated-batch fermentation for exopolysaccharide production", Biotechnology Reports (2016) 11:2-11.
Williams, J. "Growth Industry", Financial Times Jan. 12, 2019 (Mogu - Radical by Nature); download from URL <: https://mogu.bio/growth-industry-financial-times-uk-article/> in 1 page.
Woller R. "The Pearl Oyster Mushroom", University of Wisconsin Website (2011) in 2 pages.
Wösten et al., "Growing Fungi Structures in Space", ACT Research Category/Space Architecture; Noordwijk, The Netherlands (Oct. 15, 2018) in 17 pages.
Wösten et al., "How a fungus escapes the water to grow into the air", Current Biology. (1999) 9(2): 85-88.
Zeng Z., "Cosmetic composition for cleaning skin, comprises glossy ganoderma spores and collagens, content of glossy ganoderma spores in composition and content of collagens in composition", WPI/Thomson (2006-02-05) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931-938.
Collins English Dictionary, "Cavity", Definition; retrieved on Nov. 8, 2021; 1 page.
Merriam-Webster, "desiccated" (Adj.) Definition; downloaded on Nov. 8, 2021; 1 page.
Wang et al., "Chemical and structural factors influencing enzymatic saccharification of wood from aspen, birch and spruce". Biomass Bioengin. (2018) 109: 125-134.

\* cited by examiner

PROCESS FOR MAKING MINERALIZED MYCELIUM SCAFFOLDING AND PRODUCT MADE THEREBY

This application claims the benefit of Provisional Patent Application 62/667,793 filed May 7, 2018.

This invention relates to a process for making a mineralized mycelium scaffolding and product made thereby.

As is known, mineralized collagen membranes are known to be useful for various medical applications. For example, U.S. Pat. No. 6,300,315 describes a mineralized collagen membrane consisting essentially of a collagen component and a calcium phosphate minerals component and describes various processes for making the mineralized collagen membrane. Also, U.S. Pat. No. 7,514,248 describes various processes for making a composite comprising an organic fluid-swellable matrix, such as collagen, and a mineral phase, such as calcium carbonate or phosphate mineral phase, for use as a biomimetic of bone.

U.S. Pat. No. 5,532,217 describes a process for the mineralization of collagen fibers for use in bone replacement therapy and to induce repairs in bony defects.

U.S. Pat. No. 7,179,356 describes a process for preparing surfactant-polycrystalline inorganic nanostructured materials having designed microscopic patterns.

As is also known, bone implants may be provided with a coating of calcium phosphate for improved biocompatibility and bone adhesion, such as described in US 2012/0270031. Likewise, it has been known from US 2007/0196509 to use nanoscale hydroxyapatite particles for use in medical application and from US 2010/0158976 to make a collagen/hydroxyapatite composite scaffold that forms a base upon which tissue, such as cartilage, may be engineered.

Typically, the various processes for producing products as described above have required complex and time consuming steps.

Accordingly, it is an object of the invention to provide a relatively simple process for producing a mineralized biocompatible material.

It is another object of the invention to provide a unique biomedical material.

As described in published US Patent Application US 2015/0033620 (A), the environmental conditions for producing the mycological biopolymer product described therein, i.e. a high carbon dioxide ($CO_2$) content (5% to 7% by volume) and an elevated temperature (from 85° F. to 95° F.), prevent full differentiation of the fungus into a mushroom. There are no stipe, cap, or spores produced.

As described, a mycological biopolymer product consisting entirely of fungal mycelium is made by inoculating a nutritive substrate with a selected fungus in a sealed environment except for a void space, which space is subsequently filled with a network of undifferentiated fungal mycelium. The biopolymer product grows into the void space of the tool, filling the space with an undifferentiated mycelium chitin-polymer, which is subsequently extracted from the substrate and dried.

As further described in published US Patent Application US 2015/0033620 (A) the use of a lid may be used to control the localized environmental conditions influencing the growth of the mycological biopolymer.

As described in U.S. patent application Ser. No. 16/690,525, another method of growing a biopolymer material employs incubation of a growth media comprised of nutritive substrate and a fungus in containers that are placed in a closed incubation chamber with air flows passed over each container while the chamber is maintained with a predetermined environment of humidity, temperature, carbon dioxide and oxygen. The growth media in each container is incubated for a period of time sufficient for the fungus to digest the nutritive substrate and produce a mycelium biopolymer consisting entirely of fungal mycelium in each container.

Briefly, the invention provides a process wherein a scaffold of fungal biopolymer having a network of interconnected mycelia cells is initially obtained, for example, a scaffold of a mycological biopolymer made in accordance with published US Patent Application US 2015/0033620 and/or U.S. patent application Ser. No. 16/690,525.

Next, in accordance with the process, the scaffold of fungal mycelium is mineralized to apply one of a hydroxyapatite coating, calcite coating and silicate coating on the cells within the network.

The process comprises the steps of:
1. Preparing the fungal biopolymer as necessary
2. Using fungal biopolymer, functionalizing the fungal polymer to create the necessary precursor site as necessary.
3. Mineralizing the fungal biopolymer, choosing a pathway with respect to the specific mineral formation desired, including, but not limited to, silicates, apatites, and carbonates.
4. If necessary, rinse and dry material, using methods suited toward need.

EXAMPLES

1A Hydroxyapatite Mineralization of Mycelial Scaffold via a Solution-Based Reaction When low-energy hydroxyapatite $[Ca_5(PO_4)_3(OH)]$ mineralization is desired upon a bio-scaffold consisting of a cultivated mass of fungal mycelium, one should begin by preparing the mycelial mass for functionalization, taking care to preserve both the cell structure and mycelial matrix, while removing interfering/undesired constituents (cleaning while preserving structure). This will serve as the raw scaffold, upon which mineralization will occur.

The cleaned scaffold is then phosphorylated, functionalizing the chitin/chitosan backbone, replacing the —OH moiety with a phosphate group, thereby increasing the scaffold's affinity for cations to prepare the scaffold for mineralization.

The scaffold should be thoroughly rinsed of any interfering residue and is then attached to a nonreactive clip to be freely suspended in and/or imbibed with in a saturated calcium hydroxide solution for 1-30 days, depending on desired degree of calcification, purity of starting material, degree of phosphorylation, or the like. In this step, calcium penetrates the scaffold which creates the calcium phosphate precursor sites necessary for hydroxyapatite formation.

After rinsing off residual calcium hydroxide solution, the scaffold is suspended in a 36.5° C. solution with ion concentrations 1.5 times that of the human body ($1\times$=$Na^+$—142.0 mM; $K^+$—5.0 mM; $Mg^{2+}$—1.5 mM; $Ca^{2+}$—2.5 mM; $Cl^-$—148.8 mM; $HCO_3^-$—4.2 mM; $HPO_4^{2-}$—1.0 mM; trishydroxymethyl aminomethane—50 mM). The salts used to create this solution are: NaCl, $NaHCO_3$, KCl, $K_2HPO_4.3H_2O$, $MgCl_2.6H_2O$, CaCl, trishydroxymethyl aminomethane.

Once prepared, the solution is buffered to pH 7.25 with concentrated HCl. To ensure process consistency, the ion concentration should be monitored and adjusted regularly either with a chemostat or manual inspection. This step requires upwards of 30 days of active soaking of the scaffold (with or without initial imbibing) to precipitate a hydroxyapatite coating of the desired thickness on the cells of the mycelial mass of the scaffold.

The mineralized scaffold should then be dried, completing this mineralization process. The resultant scaffold of fungal biopolymer has a network of interconnected mycelia cells and a hydroxyapatite coating on the cells within the network.

1B Hydroxyapatite Mineralization of Mycelial Scaffold via a Solid-State Reaction When hydroxyapatite $[Ca_5(PO_4)_3(OH)]$ mineralization is "quickly" desired upon a bio-scaffold consisting of a cultivated mass of fungal mycelium, one should begin by preparing the mycelial mass for functionalization, taking care to preserve both the cell structure and mycelial matrix, while removing interfering/undesired constituents. This will serve as the raw scaffold, upon which mineralization will occur.

A hydroxyapatite slurry is prepared by milling calcium carbonate and dicalcium phosphate in deionized water (DI) until most agglomerated particles are destroyed.

This slurry is then dried until most residual moisture has been removed to form a desiccated powder.

The desiccated powder is then calcinated at 900° C. for 1 hour at a heating rate of 5° C./min. This reaction creates a hydroxyapatite powder.

The next step involves creating a ceramic slurry with the powder, DI water, a plasticizer (including, but not limited to, polyethylene glycol, glycerin, sorbitol, alkyl citrates, or acetylated monoglycerides), a binder (including, but not limited to: polyvinyl alcohol, lecithin, soy lecithin, or sodium stearoyl lactylate), and dispersant (including, but not limited to, polycarboxylate ether based superplasticizers, or Dispex polyacrylate dispersant).

The ceramic slurry should be created according to the following percentages: hydroxyapatite—54 wt %, DI water—33.8 wt %, plasticizer—6.2 wt %, binder—4.4 wt %, and dispersant—1.6 wt %. This is milled for 24 hours to destroy agglomerated particles.

The prepared scaffold is then imbibed with the milled ceramic slurry via vacuum infusion and lyophilized to remove moisture. The dry slurry/scaffold matrix is then sintered in a 1300° C. in a furnace for four hours at a heating rate of 5° C./min., creating a ceramic in the form of the original fungal scaffold.

The resultant ceramic consists of a scaffold of fungal biopolymer with a network of interconnected mycelia cells and a hydroxyapatite coating on at least some of the cells within the network.

1C Hydroxyapatite Mineralization of Fungal Biopolymer Scaffold via a Solution-Based Reaction When low-energy hydroxyapatite $[Ca_5(PO_4)_3(OH)]$ mineralization is desired upon a scaffold consisting of aligned bundles of fungal biopolymer assembled into a desired microstructure (e.g., helicodical to increase compressive strength by hindering crack propagation), one should begin by preparing the mycelial mass for functionalization, taking care to preserve both the cell structure and mycelial matrix, while removing interfering/undesired constituents. This will serve as the raw scaffold, upon which mineralization will occur. From here, the procedure from 1A, beginning with functionalizing the chitin/chitosan backbone, followed through completion.

The scaffolds mineralized with hydroxyapatite may be of a size and shape to be put to use as a biomedical material, for example, the scaffold may be of a flat panel shape with a thickness of 2.5 cm.

The mineralized scaffolds can be as small as 1 mm×1 mm×1 mm, and the largest piece that has been created is 15 cm×5 cm×2.5 cm.

2A Calcite Mineralization of Mycelial Scaffold Via a Solution-Based Reaction When a low-energy calcite $(CaCO_3)$ mineralization is desired upon a bio-scaffold consisting of a cultivated mass of fungal mycelium, one should begin by preparing the mycelial mass for functionalization, taking care to preserve both the cell structure and mycelial matrix, while removing interfering/undesired constituents. This will serve as the raw scaffold, upon which mineralization will occur.

A supersaturated solution is prepared from filtered and standardized stock calcium nitrate and sodium bicarbonate at 25° C. with a calcium and carbonate concentration of the working solution of $2.616 \times 10^{-3}$M. The pH of this solution is then adjusted to 8.5 with standardized 0.1M potassium hydroxide solution and this is allowed to equilibrate in temperature and $CO_2$ partial pressure.

The cleaned scaffold is then suspended in this solution, making sure the solution is fully infused into the scaffold. Ion concentrations are constantly monitored and corrected by the addition of calcium nitrate, sodium carbonate, sodium bicarbonate, and potassium hydroxide, either manually or via a pH stat.

Once the desired level of mineralization is achieved, the matrix is lyophilized to remove residual moisture and to complete the process.

3A Silication of Mycelial Scaffold Via Hydrothermal Hot Pressing

When silicate mineralization is desired upon a bio-scaffold consisting of a cultivated mass of fungal mycelium, one should begin by preparing the mycelial mass for functionalization, taking care to preserve both the cell structure and mycelial matrix, while removing interfering/undesired constituents. This will serve as the raw scaffold, upon which mineralization will occur. This prepared scaffold is then deacetylated to prepare it for mineralization.

A calcium silicate solution is created from finely ground quartz and calcium oxide, mixed well with a 1:1 Ca:Si ratio and a 20:1 water:powder ratio. The pH of this solution is adjusted to 12 with ammonium hydroxide and is transferred to a nonreactive vessel to be autoclaved at 150° C. for 24 hours to create calcium silicate, likely xonotlite $[Ca_6Si_6O_{17}(OH)_2]$.

The silicate product is then collected, washed with DI water, and dried for 24 hours to remove residual water. The dry silicate powder is then mixed well into a 90 wt % slurry with DI water and is then infused into the prepared scaffold at a slurry:scaffold ratio of 20:1.

The scaffold/slurry matrix is then moderately compressed (upwards of 50 MPa) and returned to the autoclave at 150° C. for upwards of 2 hours. The mineralized product is then dried to complete the process.

3B Silication of Mycelial Scaffold Via a Solution-based Reaction

When silicate mineralization is desired upon a bio-scaffold consisting of a cultivated mass of fungal mycelium, one should begin by preparing the mycelial mass for functionalization, taking care to preserve both the cell structure and mycelial matrix, while removing interfering/undesired constituents. This will serve as the raw scaffold, upon which mineralization will occur.

This prepared scaffold is then deacetylated to prepare the scaffold for functionalization.

The deacetylation step removes the primary amine from chitin, which cannot be functionalized, and transitions the functional group to a hydroxyl, which is chitosan. This hydroxyl can then serve as the targeted site for phosphorylation or the like.

The deacetylation process uses a 5 molar concentration of NaOH at 90 C for 30 to 120 minutes. The specimen is immersed in solution during this time.

The deacetylated scaffold, under air or an inert atmosphere, is then imbibed with catalytic agent (including, but not limited to, an appropriate concentration and type of acid [e.g., acetic acid, hydrochloric acid, phosphoric acid, or the like], fluoride salts (e.g., potassium fluoride, sodium fluoride, tetra-n-butylammonium fluoride, or like like), water, an amino acid (e.g., cysteine or the like) or an amine [e.g., urea, imidazole, or the like]).

The catalyst/scaffold matrix is then infused with tetraethylorthosilicate and silica allowed to condense onto the scaffold for upwards of 24 hours. The product is then dried to complete the process.

The invention thus provides a relatively simple process for producing a mineralized biocompatible material as well as a unique biomedical material that may be used for medical applications in place of mineralized collagen membranes and collagen/hydroxyapatite composite scaffolds.

What is claimed is:

1. A structure comprising
   a scaffold of fungal biopolymer of predetermined form characterized in being formed of a network of interconnected mycelia cells; and
   a coating of at least one of an apatite, a carbonate, and a silicate on at least some of said cells within said network.

2. The structure of claim 1, wherein said predetermined form is a flat panel shape.

3. The structure of claim 2, wherein said flat panel shape has a thickness of 2.5 cm.

4. The structure of claim 1, wherein said coating is one of a hydroxyapatite, calcite, and silicate.

5. The structure of claim 1, wherein said coating is a ceramic made from hydroxyapatite powder, water, a binder, a plasticizer, and a dispersant.

6. The structure of claim 1, wherein said fungal biopolymer of said scaffold consists of aligned bundles of fungal biopolymer assembled into a predetermined microstructure.

7. The structure of claim 1, wherein said coating is made from dried calcium silicate powder and water.

8. The structure of claim 1, wherein said coating is made from a solution of catalytic agent, fluoride salts, water, and one of an amino acid and an amine.

9. The structure of claim 8, wherein said coating is infused with tetraethylorthosilicate.

10. The structure of claim 1, wherein said fungal biopolymer of said scaffold has a chitin/chitosan backbone.

11. The structure of claim 10, wherein an —OH moiety in said scaffold is replaced with a phosphate group.

12. The structure of claim 11, wherein said coating is a ceramic made from hydroxyapatite powder, water, a binder, a plasticizer, and a dispersant.

* * * * *